United States Patent [19]

Tesmann et al.

[11] 4,226,852

[45] * Oct. 7, 1980

[54] TWO-COMPONENT PEROXIDE HAIR BLEACHING COMPOSITIONS

[75] Inventors: Holger Tesmann, Düsseldorf; Erwin Weinrich, Haan; Edgar Lieske, Düsseldorf, all of Fed. Rep. of Germany

[73] Assignee: Henkel Kommanditgesellschaft auf Aktien, Düsseldorf-Holthausen, Fed. Rep. of Germany

[*] Notice: The portion of the term of this patent subsequent to Jan. 29, 1997, has been disclaimed.

[21] Appl. No.: 27,512

[22] Filed: Apr. 5, 1979

Related U.S. Application Data

[63] Continuation-in-part of Ser. No. 873,219, Jan. 30, 1978.

[30] Foreign Application Priority Data

Feb. 5, 1977 [DE] Fed. Rep. of Germany ....... 2704905

[51] Int. Cl.$^2$ ............................................. A61K 7/135
[52] U.S. Cl. .......................................... 424/62; 8/111; 132/7; 252/186; 424/DIG. 3
[58] Field of Search ............... 8/111; 424/DIG. 3, 62; 252/186; 132/7

[56] References Cited

U.S. PATENT DOCUMENTS

| | | | |
|---|---|---|---|
| 3,152,181 | 10/1964 | Shapiro et al. | 424/62 X |
| 3,812,247 | 5/1974 | Heinz et al. | 424/62 |
| 3,816,614 | 6/1974 | Zeffren et al. | 424/62 |
| 3,931,912 | 1/1976 | Hsiung | 424/62 X |

*Primary Examiner*—Allen J. Robinson
*Attorney, Agent, or Firm*—Hammond & Littell, Weissenberger and Muserlian

[57] ABSTRACT

A two-component composition for bleaching hair comprising a peroxide oxidation agent, an ammonia-free alkalinization agent and a guanidine derivative of the formula

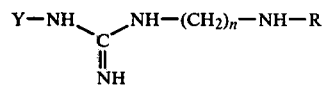

as bleaching accelerator, wherein R is hydrogen,

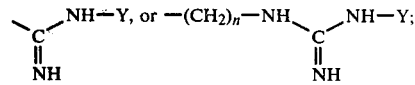

Y is hydrogen, NH$_2$ or akyl having 1 to 4 carbon atoms, and n is 2 or 3, or an acid addition salt thereof.

3 Claims, No Drawings

TWO-COMPONENT PEROXIDE HAIR BLEACHING COMPOSITIONS

CROSS-REFERENCE TO RELATED APPLICATION

This is a continuation-in-part of copending United States patent application Ser. No. 873,219, filed Jan. 30, 1978.

BACKGROUND OF THE INVENTION

Hair-bleaching agents based on a peroxide oxidation agent, such as hydrogen peroxide, urea peroxide, melamine perhydrate, etc. are generally used for the bleaching of human hair. A disadvantage of these peroxide bleaching agents is that they have to be used in an alkaline medium. Aqueous ammonia is generally used to adjust the required pH value and at the same time accelerates the oxidative destruction of the particles of the hair pigment (melanosomes). However, a considerable disadvantage is the highly irritating effect which ammonia has on the skin and mucous membranes and the unpleasant odor of ammonia which cannot be masked even by perfuming. Thus it became desirable to replace ammonia by odorless alkalinization agents such as alkali metal hydroxides, magnesium oxide or by alkanolamines and to further accelerate the bleaching process in order to avoid the disadvantages of ammonia on the one hand and, on the other hand, to minimize the oxidative damage to the hair. The bleaching accelerators used must, furthermore, be toxicologically compatible.

Therefore, the task arose of providing new compositions for bleaching hair which are based on peroxide oxidation agents and ammonia-free alkalinization agents and which do not have the aforesaid disadvantages.

OBJECTS OF THE INVENTION

An object of the present invention is to develop an agent for accelerating the bleaching of hair by peroxide oxidation agents which minimizes the oxidative damage to the hair and does not lead to irritation of the skin.

Another object of the present invention is the development of a composition for bleaching hair, containing a peroxide oxidation agent, an ammonia-free alkalinization agent and, as bleaching accelerator, a guanidine derivative of the formula

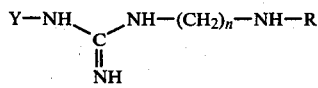

wherein R is hydrogen, the radical

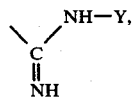

or the radical

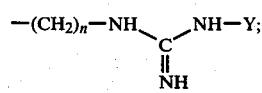

Y is hydrogen, the NH$_2$ radical or, an alkyl radical having 1 to 4 carbon atoms, and n is the integer 2 or 3, or an acid addition salt thereof.

A further object of the present invention is the development of a method of accelerating the bleaching of hair through use of peroxide oxidation agents and ammonia-free alkalinization agents by means of said bleaching accelerator described above.

These and other objects of the present invention will become more apparent as the description thereof proceeds.

DESCRIPTION OF THE INVENTION

Accordingly the present invention provides compositions for the bleaching of hair based on peroxide oxidation agents and ammonia-free alkalinization agents and containing, as bleaching accelerators, guanidine derivatives of the formula

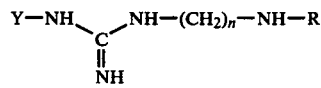

wherein R is a member selected from the group consisting of hydrogen, the radical

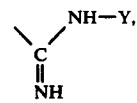

and the radical

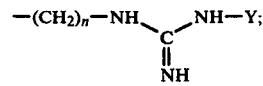

Y is a member selected from the group consisting of hydrogen, the NH$_2$ radical, and an alkyl radical having 1 to 4 carbon atoms, and n is the integer 2 or 3, or acid addition salts thereof.

More particularly, the present invention relates to a two-component composition for bleaching hair comprising (A) a mixture of a guanidine derivative of the formula

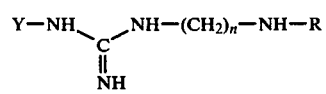

wherein R is a member selected from the group consisting of hydrogen, the radical

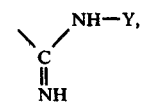

and the radical

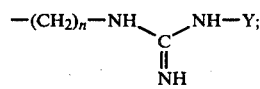

Y is a member selected from the group consisting of hydrogen, the $NH_2$ radical, and an alkyl radical having 1 to 4 carbon atoms, and n is the integer 2 or 3, or acid addition salts thereof, thickeners, surfactants, alkalinization agents, perfume oils and, optionally, ethylene diurea and catalytic quantities of a heavy metal, and (B) a peroxide oxidation agent and, optionally, small quantities of a stabilizer. Components A and B are separately packaged and mixed together by the user immediately before application to the hair.

The guanidine derivatives which are used in accordance with the invention as bleaching accelerators, are known in the literature. They can be produced as hydrochlorides from equivalent quantities of the starting materials in accordance with the method given hereinafter. Thus, for example, the N,N'-diamino-ethylene-bis-guanidinium chloride can be produced in accordance with the method given by A.F. McKay et al. in J. Med. Chem. 6, 587 (1963), by reacting S-methyl-isothiuronium chloride with ethylenediamine in accordance with the following reaction scheme:

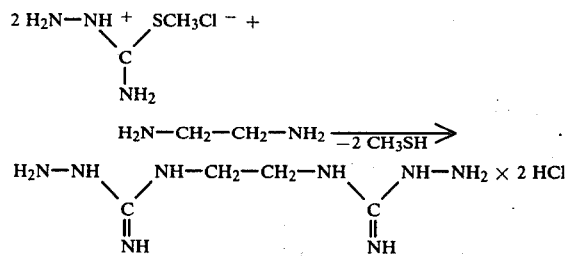

Further data for producing analogous compounds are given by M. Schenck and H. Kirchhof in H.S. Zeitschr. physiol. Chem. 155, 306 (1926).

Data for the production of ethylene-bis-guanidinium chloride and 1-amino-3-guanidino-propane-dihydrochloride are given by K. Sugino, K. Sjirai, K. Aoyagi in Bull. Soc. Chem. Japan 17, 126 (1942). The reactions take place in accordance with the following schemes.

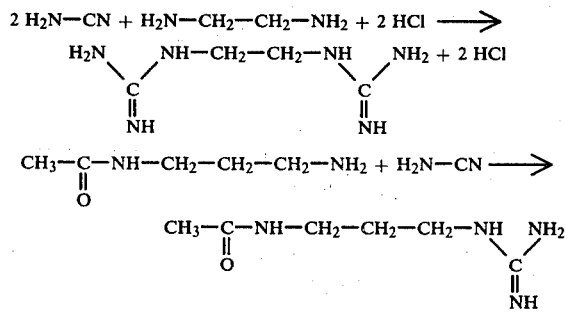

Examples of the guanidine compounds which are used in accordance with the invention as bleaching accelerators, are 2-aminoethyl-guanidine, 3-aminopropyl-guanidine, 2-aminoethyl-(N-amino)-guanidine, 2-aminoethyl-(N-methyl)-guanidine, 3-aminopropyl-(N-ethyl)-guanidine, ethylene-bis-guanidine, propylene-bis-guanidine, ethylene-bis-(1-aminoguanidine), di-(2-guanidinoethyl)-amine.

Advantageously, the guanidine compounds, which are used in accordance with the invention as bleaching accelerators, are used in the form of their salts with inorganic acids such as hydrochloric acid, sulfuric acid, nitric acid, phosphonic acid, carbonic acid, or organic acids such as formic acid, acetic acid, propionic acid, succinic acid, tartaric acid, and citric acid. The quantity of guanidine compound to be used in accordance with the invention varies between 0.1 to 10 percent by weight, preferably 0.5 to 3 percent by weight, relative to the total bleaching agent.

A particularly satisfactory bleaching action can be obtained when the guanidine compounds in accordance with the invention are used in combination with ethylene diurea. The quantity of ethylene diurea lies between 0.2 to 20 percent by weight, preferably 0.5 to 5 percent by weight, relative to the total bleaching agent.

The bleaching process can be further accelerated when catalytic quantities of heavy metal ions, such as iron or copper, are added to the bleaching solutions in accordance with the invention.

The peroxide oxidation agent of the invention can be any type of inorganic or organic peroxide which will release active oxygen in an aqueous solution. Preferably, hydrogen peroxide is used as a peroxide component in the hair bleaching agents in accordance with the invention. Alternatively, however, it may be replaced by sodium peroxide, potassium peroxide, sodium perborate, sodium percarbonate or its organic compounds of addition such as urea peroxide or melamine perhydrate. The concentration of peroxides, calculated as hydrogen peroxide, should be from 2 to 8 percent by weight, preferably from 4 to 6 percent by weight, relative to the total bleaching agent.

Thickening agents, which impart a creamy consistency to the products of the invention, are generally added to the hair bleaching agents in order to facilitate the practical use thereof. A number of products are known to the cosmetician for this purpose, such as cellulose derivatives like carboxymethyl cellulose, emulsions of fatty alcohols, various polymers, sodium metasilicate and others. Their concentration can vary within wide limits and will generally be between 1 to 10 percent by weight, relative to the total bleaching agent. In addition, the hair bleaching agents in accordance with the invention generally contain approximately 1 to 10 percent by weight, relative to the total agent, of a surface-active compound, although its presence is not essential.

The hair bleaching agents in accordance with the invention are made up in the form of a two-component package, the two components of which can be mixed by the user directly before being applied to the hair. The guanidine compounds of the invention in combination with the thickeners, surfactants, alkalinization agents, perfume oils and, if desired, ethylene diurea and/or catalytic quantities of a heavy metal constitute one component in the form of a paste, cream, emulsion or a powder, while the other component contains the peroxide compound to which, if desired, are added small quantities of a stabilizer such as acetophosphonic acid, ethylenediaminetetraacetate, -phosphate or -citrate.

Any ammonia-free alkalinization agent can be used in the hair bleaching compositions of the invention. Suitable alkalinization agents include alkali metal hydroxides, magnesium oxide and alkanolamines, such as ethanolamine. The concentration of the ammonia-free alkalinization agents is sufficient to give an alkaline pH to the hair bleaching compositions of the invention. The hair bleaching agents of the invention can contain, for example, from about 1 to 20 percent by weight, relative to the total agent, of the ammonia-free alkalinization agent.

Water generally acts as the solvent in the hair bleaching process, although, alternatively, it can be partially replaced, as e.g. by up to 20 weight %, by lower alcohols such as ethanol, isopropanol or glycerol, or mixtures thereof. Water can advantageously constitute, for example, from about 10 to 70 percent by weight, relative to the total bleaching agent.

The bleaching process generally lasts 15 to 30 minutes, although shorter or longer bleaching times are possible according to the desired intensity of the bleaching. In addition to their effect with respect to accelerating the bleaching operation, the guanidine compounds which are used in accordance with the invention are also distinguished by the fact that, owing to their satisfactory toxicological compatibility, they do not lead to irritation of the skin.

The hair bleaching compositions of the invention can thus contain (a) 0.1% to 10%, preferably 0.5% to 3%, by weight of a guanidine derivative of the formula

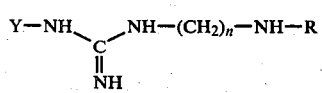

wherein R is a member selected from the group consisting of hydrogen, the radical

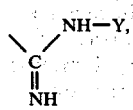

and the radical

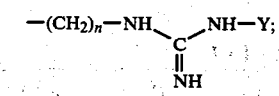

Y is a member selected from the group consisting of hydrogen, the NH$_2$ radical, and an alkyl radical having 1 to 4 carbon atoms, and n is the integer 2 or 3, or a water-soluble acid addition salt thereof, (b) 1% to 20%, by weight of an ammonia-free alkalinization agent, (c) 2% to 8%, preferably 4% to 6%, by weight, calculated as hydrogen peroxide, of a peroxide oxidation agent, (d) 0 to 20%, preferably 0.2% to 20%, more preferably 0.5% to 5%, by weight of ethylene diurea, (e) 0 to 0.01 mole/liter of heavy metal cations, (f) 0 to 10%, preferably 1% to 10%, by weight of thickening agents, (g) 0 to 10%, preferably 1% to 10%, by weight of surface active agents, (h) 0 to 0.1% by weight of a peroxide stabilizer, (i) 0 to 2% by weight of additional conventional ingredients, such as perfume oils, and (j) 10% to 70% by weight of solvent, preferably water, the content of the ammonia-free alkalinization agent being sufficient to give the solution a pH of 8–10.5.

The invention also includes a two-component hair bleaching composition wherein one component separately packaged can contain the above ingredients (a), (b), (d), (e), (f), (g), (i) and (j) and the other component can contain the above ingredients (c), (h) and (j). The solvent can be present, if desired, in both components of the twocomponent composition. However, it is always present in the peroxide component. The amount of solvent which should suitably be present in either component of the hair bleaching composition is readily determinable by those skilled in the art. The two components are premixed just prior to the application of the composition to the hair in the customary manner.

In another embodiment of the invention there is provided a composition which can contain all the above ingredients of the above first-mentioned component of the two-component composition of the invention, i.e., a hydrous or anhydrous composition but without any peroxide oxidation agent or its stabilizer. The oxidation agent, and its optional stabilizer, is admixed thereto just prior to application of this composition to the hair in customary manner.

The invention also provides a method of bleaching hair which comprises contacting human hair, at a temperature of from 20° C. to 45° C., with an aqueous liquid containing a peroxide oxidation agent, an ammonia-free alkalinization agent and, as a bleaching accelerator, a guanidine derivative of the formula

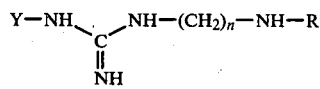

wherein R is a member selected from the group consisting of hydrogen, the radical

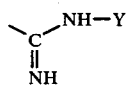

and the radical

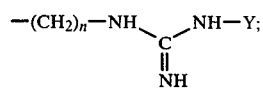

Y is a member selected from the group consisting of hydrogen, the NH$_2$ radical, and an alkyl radical having 1 to 4 carbon atoms, and n is the integer 2 or 3, or acid addition salts thereof.

Non-substituted and alkyl-substituted guanidinium salts have been variously proposed in the patent literature for use in bleaching agents. However, it has transpired that, in practice, the effect of such additives is minimal. On the other hand, considerable acceleration of the bleaching process can be obtained with the guanidine derivatives to be used in accordance with the invention, even without the addition of persalts. A guanidino group in the said guanidine derivatives of the invention is attached by way of a bridge of two or three carbon atoms to a further group containing nitrogen, namely, an aminoor guanidino group. The bleaching acceleration is perceptibly poorer in the presence of four bridge carbon atoms, such as in the case of arginine or butylene-bis-guanidine, and lies in the range of the action of ammonia or the less effective guanidine itself.

The present invention will now be further described by means of the following examples which are not to be limitative in any manner.

EXAMPLES

1. PRODUCTION OF THE GUANIDINE COMPOUNDS

The production of some of the guanidine compounds which are used in accordance with the invention, and which are presented in the following tests and formulations, will be described in the first instance.

I. Propylene-bis-guanidinium chloride 63.3 gm (0.5 mole) of S-methylisothiourea chloride were dissolved in 350 ml of water and 18.5 gm (0.25 mole) of propylene diamine were added thereto. The reaction mixture was reduced in vacuo after agitation for 24 hours at room temperature, and the residue was recrystallized from methanol. 49 gm of propylene-bis-guanidinium chloride (85% of the theoretical yield), having a m.p. of 195° to 200° C., were obtained.

The following compounds were produced in an analogous manner by using the appropriate starting materials in each case.

II. Butylene-bis-guanidinium chloride
(Yield 80% of theory, m.p. 236° C.)

III. Ethylene-bis-(1-aminoguanidinium) chloride
(Yield 45% of theory, m.p. 240° C. decomposition.)

IV. Di-2-guanidinoethylamine-dihydrochloride
(Yield 85% of theory, m.p. 230° C. decomposition.)

V. 3-Aminopropul-guanidinium chloride 444 gm (6 mole) of propylenediamine and 176 gm (2 mole) of ethyl acetate were reacted for 30 hours at 100° C. in an autoclave. After filtration and reduction, 150 gm of acetylpropylene diamine having a boiling point of 115° C./1 mm and a refractive index $n_D^{20}=1.4903$ were obtained by distillation.

46.4 gm (0.4 mole) of acetylpropylenediamine were neutralized with an equivalent quantity of 2N hydrochloric acid. 16 gm (0.4 mole) of cyanamide were then added and the pH value was adjusted to 7. The mixture was acidified with semi-concentrated hydrochloric acid after boiling for two hours and was refluxed for five hours. The mixture was subsequently evaporated in vacuo, and the residue was recrystallized from isopropanol/water. 28.7 gm, that is 39% of theory, of 3-amino-propyl-guanidinium chloride having a m.p. of 249° to 250° C. were obtained.

VI. 3-aminoethyl-guanidinium chloride

This compound was produced, by a method analogous to that described in V above, from acetylethylenediamine with a yield of 61% of theory. M.P. 210° C. under sublimation.

VII. Ethylene-bis-guanidinium chloride 63 gm (1.5 mole) of cyanamide and 99 gm (0.75 mole) of ethylenediamine dihydrochloride were dissolved in 1.2 liters of ethanol and 300 ml of water and were refluxed for four hours. After evaporation of the solvent, recrystallization was effected from ethanol/ether. 120 gm of ethylene-bis-guanidinium chloride, that is, 74% of theory, were obtained and had a m.p. of 228° to 230° C.

2. TEST OF TECHNICAL ACTIVITY

I. Acceleration of the bleaching process

The hydrochlorides of guanidine, 1-aminoguanidine and arginine, which are used as comparison substances in the following test, are commercially available products.

The values given in the following Tables 1 and 2 constitute the measurement results of a test in which the bleaching process was observed photometrically in aqueous suspensions of melanosomes. Melanosomes can be isolated from hair in accordance with the method given by J. Barovansky and P. Hach, published in Dermatologica 145, 37 (1972).

The melanosome suspension is mixed in the measuring vessel of a photometer with a bleaching solution which contains hydrogen peroxide, an alkalinization agent (sodium hydroxide) and the bleaching accelerator, and the stray light (wavelength 400 nm) passing through is recorded in dependence upon time. The time $t_{2/3}$, in which the attenuance of light has reduced to $\frac{2}{3}$ of the original attenuance, is measured as the characteristic value of the speed of the course of the bleaching operation.

The values given in the following Table 1 were obtained in this test.

TABLE 1

ACCELERATION OF THE BLEACHING PROCESS
Conditions of the test solution:
8% $H_2O_2$; pH 8.85 to 8.95; Room temperature;
Melanosomes 0.25 mg/ml.

| 0.063 m Substance/l | $t_{2/3}$ (minutes) |
|---|---|
| Blank value | 12.6 |
| $NH_3$ | 7.0 |
| $H_2N-C(=NH)-NH_2 \times HCl$ | 10.2 |
| $H_2N-C(=NH)-NH-NH_2 \times HCl$ | 9.2 |
| $H_2N-C(=NH)-NH-CH_2-CH_2-CH_2-CH_2-NH-C(=NH)-NH_2 \times 2 HCl$ | 8.8 |

TABLE 1-continued

ACCELERATION OF THE BLEACHING PROCESS
Conditions of the test solution:
8% $H_2O_2$; pH 8.85 to 8.95; Room temperature;
Melanosomes 0.25 mg/ml.

| 0.063 m Substance/l | $t_{2/3}$ (minutes) |
|---|---|
| $H_2N-C(=NH)-NH-CH_2-CH_2-CH_2-CH(COOH)-NH_2$ | 8.2 |
| $H_2N-C(=NH)-NH-CH_2-CH_2-NH_2 \times 2\,HCl$ | 2.5 |
| $H_2N-C(=NH)-NH-CH_2-CH_2-CH_2-NH_2 \times 2\,HCl$ | 4.2 |
| $H_2N-C(=NH)-NH-CH_2-CH_2-NH-C(=NH)-NH_2 \times 2\,HCl$ | 0.5 |
| $H_2N-C(=NH)-NH-CH_2-CH_2-CH_2-NH-C(=NH)-NH_2 \times 2\,HCl$ | 0.5 |
| $H_2N-NH-C(=NH)-NH-CH_2-CH_2-NH-C(=NH)-NH-NH_2 \times 2\,HCl$ | 1.0 |
| $H_2N-C(=NH)-NH-CH_2-CH_2-NH-CH_2-CH_2-NH-C(=NH)-NH_2 \times 2\,HCl$ | 3.9 |

Table 1 shows the greatly accelerative effect which the guanidine compounds, which are used in accordance with the invention, have on the bleaching process.

II. Influence of heavy metal ions on the activation of the bleaching process

The effect of heavy metal ions on the activation of the bleaching process in aqueous suspensions of melanosomes was investigated in a further test. The results are given in the following Table 2.

TABLE 2

INFLUENCE OF HEAVY METAL IONS ON THE ACTIVATION OF THE BLEACHING PROCESS
Conditions of the test solution:
8% $H_2O_2$; pH 8.97 to 8.92; Room temperature
Melanosomes 0.25 mg/ml

| | Test Solution | $CuCl_2$ | $FeSO_4$ |
|---|---|---|---|
| Ligand | Metal ion concentration Mole/l | Additive $t_{2/3}$(min) | Additive $t_{2/3}$(min) |
| Blank value ($H_2O$) | — | 12.4 | 12.6 |
| | $10^{-5}$ | 9.3 | 9.6 |
| | $10^{-4}$ | 5.5 | 7.7 |
| | $5 \times 10^{-4}$ | 4.8 | — |
| | $10^{-3}$ | — | 6.2 |
| 0.025 m $NH_3$/l | — | 11.9 | 11.9 |
| | $10^{-5}$ | 8.2 | 8.9 |
| | $10^{-4}$ | 3.9 | 5.6 |
| | $5 \times 10^{-4}$ | 3.1 | — |
| | $10^{-3}$ | — | 4.2 |
| 0.0125 m /l $H_2N-C(=NH)-NH-CH_2-CH_2-NH-C(=NH)-NH_2$ | — | 10.9 | 10.9 |
| | $10^{-5}$ | 8.6 | 9.2 |
| | $10^{-4}$ | 2.1 | 3.9 |
| | $5 \times 10^{-4}$ | 1.8 | — |

TABLE 2-continued

INFLUENCE OF HEAVY METAL IONS ON THE
ACTIVATION OF THE BLEACHING PROCESS
Conditions of the test solution:
8% $H_2O_2$; pH 8.97 to 8.92; Room temperature
Melanosomes 0.25 mg/ml

| Ligand | Test Solution Metal ion concentration Mole/l | $CuCl_2$ Additive $t_{2/3}$(min) | $FeSO_4$ Additive $t_{2/3}$(min) |
|---|---|---|---|
| | $10^{-3}$ | — | 2.9 |

Table 2 shows the accelerative effect of the heavy metal ions.

III. Toxicological compatibility

The following values were obtained by investigating the toxicological compatibility of ethylene-bis-guanidine-dihydrochloride.

(a) Acute toxicity

Mouse, oral, one administration with a probang, three animals each dose, observation time 24 hours. $LD_{50}$ 625 mg/kg.

(b) Skin compatibility

Hairless mouse, one application, three test animals per concentration, observation time 24 hours. 1% and 5% without result. 25% slight reddening of the skin.

(c) Skin compatibility

Hairless mouse, repeated application, once daily for ten days. 5% and 10% without result.

(d) Mucous membrane compatibility

Rabbit's eye, drops of 5% solution applied once, contact time 30 seconds, then washed out with lukewarm water; no result.

The above data shows the satisfactory toxicological compatibility of the substances to be used in accordance with the invention.

3. BLEACHING AGENTS OF THE INVENTION

Some examples of the hair bleaching agents of the invention are given hereinafter.

EXAMPLE 1

Bleaching Cream

| Component I: | Parts by Weight |
|---|---|
| Cetylstearyl alcohol | 20 |
| Sodium-cetylstearyl sulfate | 12 |
| Fatty alcohol polyglycol ether | 2 |
| Decyl oleate | 5 |
| Ethanolamine | 4 |
| Ethylene diurea | 3 |
| Ethylene-bis-guanidinium-dihydrochloride | 2 |
| Water | 52 |
| | 100 |
| Component II: | |
| 11% $H_2O_2$ solution | 100 |

EXAMPLE 2

Bleaching Emulsion

| Component I: | Parts by Weight |
|---|---|
| Cetylstearyl alcohol | 2 |
| Decyl oleate | 3 |
| Lanolin | 2 |
| Ethanolamine | 4 |
| Ethylene diurea | 3 |
| Ethylene-bis-guanidinium-dihydrochloride | 2 |
| Water | 84 |
| | 100 |
| Component II: | |
| 11% $H_2O_2$ solution | 100 |

EXAMPLE 3

Bleaching Powder

| Component I: | Parts by Weight |
|---|---|
| Magnesium hydrocarbonate | 51 |
| Magnesium oxide | 28 |
| Potassium sulfate | 5 |
| Ammonium sulfate | 5 |
| Sodium lauryl sulfate | 3 |
| Polymethacrylate | 2 |
| Ethylene diurea | 3 |
| Ethylene-bis-guanidinium-dihydrochloride | 3 |
| | 100 |
| Component II: | |
| 11% $H_2O_2$ solution | 100 |

Instead of the ethylene-bis-guanidinium-dihydrochloride used in the above examples, any of the other guanidine compounds of the invention can be used with equally satisfactory results.

EXAMPLE 4

Bleaching Cream Pack

| Component I: | Parts by Weight |
|---|---|
| Ethylene-bis-guanidinium dihydrochloride | 2.0 |
| Ethanolamine | 5.0 |
| Ethylene urea | 4.0 |
| Copper sulfate | 0.01 |
| Cetylstearyl alcohol | 20.0 |
| Sodium cetylstearyl sulfate | 15.0 |
| Ammonium sulfate | 2.0 |
| Water | 51.99 |
| | 100.0 |
| Component II: | |
| 25% $H_2O_2$ solution | 45.0 |
| Hexahydroxyethane diphosphonic acid | 2.0 |
| Water | 53.0 |
| | 100.0 |

Before use, the components are mixed in a ratio of about 1:1. Depending on the amount of hair, etc., between about 75 and 150 gm, on the average about 100 gm, of the mixed cream are generally used for a treatment.

EXAMPLE 5

Bleaching Cream Pack

| Component I: | Parts by Weight |
| --- | --- |
| Propylene-bis-guanidinium hydrochloride | 3.0 |
| Diethanolamine | 6.0 |
| Ethylene urea | 3.0 |
| Iron (II)-sulfate | 0.01 |
| Octylstearyl alcohol | 25.0 |
| Sodium-decylstearyl sulfate | 17.0 |
| Ammonium sulfate | 1.0 |
| Water | 44.99 |
|  | 100.0 |
| Component II: |  |
| 25% $H_2O_2$ solution | 35.0 |
| Ethylenediaminetetraacetic acid | 2.0 |
| Water | 63.0 |
|  | 100.0 |

Before use, the components are mixed in a ratio of about 1:1. The average consumption for a treatment is again about 100 gm of the mixed cream.

EXAMPLE 6

Bleaching Cream Pack

| Component I: | Parts by Weight |
| --- | --- |
| 3-Aminopropyl guanidinium chloride | 6.0 |
| Ethanolamine | 2.0 |
| Diethanolamine | 2.0 |
| Ethylene urea | 2.0 |
| Nickel sulfate | 0.01 |
| $C_{12}$—$C_{18}$ fatty alcohol | 30.0 |
| Sodium cetylstearyl sulfate | 15.0 |
| Ammonium sulfate | 3.0 |
| Water | 39.99 |
|  | 100.0 |
| Component II: |  |
| 25% $H_2O_2$ solution | 30.0 |
| 2-Phosphonobutane-1,2,4-tricarboxylic acid | 1.0 |
| Water | 69.0 |
|  | 100.0 |

Before use, the components are mixed in a ratio of about 1:1. The average consumption for a treatment is about 100 gm of the mixed cream.

EXAMPLE 7

Bleaching Cream Pack

| Component I: | Parts by Weight |
| --- | --- |
| Butylene-bis-guanidinium chloride | 4.0 |
| Diethanolamine | 4.0 |
| Ethylene urea | 5.0 |
| Iron (II)-sulfate | 0.02 |
| $C_{12}$—$C_{18}$ fatty alcohol | 20.0 |
| Sodium cetylstearyl sulfate | 5.0 |
| Ammonium sulfate | 1.0 |
| Water | 60.98 |
|  | 100.0 |
| Component II: |  |
| 25% $H_2O_2$ solution | 40.0 |
| Hexahydroxyethane diphosphonic acid | 1.0 |
| Water | 59.0 |
|  | 100.0 |

Before use, the components are mixed in a ratio of about 1:1. The average consumption for a treatment is about 100 gm of the mixed cream.

The preceding specific embodiments are illustrative of the practice of the invention. It is to be understood, however, that other expedients known to those skilled in the art, or disclosed herein may be employed without departing from the spirit of the invention or the scope of the appended claims.

We claim:

1. A two-component composition for bleaching hair comprised of:

I. a first component consisting essentially of an admixture of:

(a) 0.1 to 10 percent by weight of a guanidine derivative of the formula:

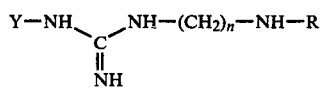

wherein R is a member selected from the group consisting of hydrogen, the radical

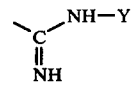

and the radical

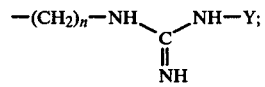

Y is a member selected from the group consisting of hydrogen, the $NH_2$ radical, and an alkyl radical having 1 to 4 carbon atoms, and n is the integer 2 or 3, or a water soluble acid addition salt thereof, (b) 1 to 20 percent by weight of an ammonia-free alkalinization agent in an amount sufficient to give the composition a pH of 8–10.5, (c) 0 to 20 percent by weight of ethylene diurea, (d) 0 to 0.01 mole/liter of heavy metal cations, (e) 0 to 10 percent by weight of thickening agents, (f) 0 to 10 percent by weight of surface-active agents, (g) 0 to 2 percent by weight of additional conventional ingredients, and (h) 0 to 70 percent by weight of solvent; and II. a second component for admixture with said first component consisting essentially of an admixture of:

(a) 2 to 8 percent by weight, calculated as hydrogen peroxide, of a peroxide oxidation agent, (b) 0 to 0.1 percent by weight of a peroxide oxidant stabilizer, and (c) up to 70 percent by weight of solvent, the total amount of solvent in both components being from 10 to 70 percent by weight.

2. A hair bleaching acceleration composition consisting essentially of the first component of claim 1.

3. A method of bleaching human hair which comprises the step of contacting said human hair with the admixed two components of claim 4 in a ratio of about 1:1, at a temperature of from 20° to 45° C. in an effective amount to bleach said hair.

* * * * *

UNITED STATES PATENT AND TRADEMARK OFFICE
CERTIFICATE OF CORRECTION

PATENT NO. : 4,226,852
DATED : October 7, 1980
INVENTOR(S) : HOLGER TESMANN ET AL.

It is certified that error appears in the above—identified patent and that said Letters Patent is hereby corrected as shown below:

Column 2, line 1: "radical or, an alkyl" should read
-- radical, or an alkyl --.

Column 3, line 51: The portion of the formula which reads
"+ 2 HCl" should read -- x 2 HCl --.

line 62, after the last formula, please insert:

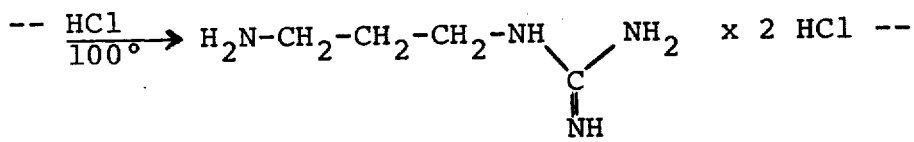

Column 6, line 10: "twocomponent" should read
-- two-component --.

Column 14, line 65: "claim 4" should read -- claim 1 --.

Signed and Sealed this

Twenty-eighth Day of July 1981

[SEAL]

Attest:

GERALD J. MOSSINGHOFF

Attesting Officer    Commissioner of Patents and Trademarks